(12) United States Patent
Colomb-Delsuc et al.

(10) Patent No.: US 11,125,672 B2
(45) Date of Patent: Sep. 21, 2021

(54) METHOD OF QUANTITATIVE MEASUREMENT OF PARTICLE CONTENT USING HYDRATED STATE IMAGING

(71) Applicant: Intelligent Virus Imaging Inc., Southern Pines, NC (US)

(72) Inventors: Mathieu Colomb-Delsuc, Älvsjo (SE); Lars Haag, Nykvarn (SE); Rickard Nordström, Tullinge (SE); Martin Ryner, Huddinge (SE)

(73) Assignee: INTELLIGENT VIRUS IMAGING INC., Southern Pines, NC (US)

( * ) Notice: Subject to any disclaimer, the term of this patent is extended or adjusted under 35 U.S.C. 154(b) by 0 days.

(21) Appl. No.: 16/326,358

(22) PCT Filed: Jan. 25, 2018

(86) PCT No.: PCT/US2018/015263
§ 371 (c)(1),
(2) Date: Feb. 18, 2019

(87) PCT Pub. No.: WO2018/160298
PCT Pub. Date: Sep. 7, 2018

(65) Prior Publication Data
US 2019/0331584 A1 Oct. 31, 2019

Related U.S. Application Data

(60) Provisional application No. 62/465,981, filed on Mar. 2, 2017.

(51) Int. Cl.
| | |
|---|---|
| *C12N 7/00* | (2006.01) |
| *G01N 1/38* | (2006.01) |
| *G01N 15/10* | (2006.01) |
| *C12Q 1/70* | (2006.01) |

(52) U.S. Cl.
CPC .............. *G01N 15/10* (2013.01); *C12N 7/00* (2013.01); *C12Q 1/70* (2013.01); *G01N 1/38* (2013.01); *C12N 2750/14121* (2013.01); *C12N 2750/14123* (2013.01)

(58) Field of Classification Search
CPC .......... G01N 15/10; G01N 1/38; G01N 15/14; G01N 15/1468; G01N 1/4077; G01N 2015/1486; G01N 15/0625; G01N 2015/1006; G01N 2015/1093; G01N 2223/401; G01N 15/1475; G01N 2015/0038; G01N 2223/405; G01N 30/52; G01N 1/2806; G01N 33/56983; C12N 7/00; C12N 2750/14121; C12N 2750/14123; C12N 2795/18123; C12N 15/88; C12N 15/11; C12N 15/85; C12N 15/907; C12N 2310/20; C12N 2510/00; C12N 11/10; C12N 11/14; C12N 15/52; C12N 15/63; C12N 15/67; C12N 15/86; C12N 1/36; C12N 2501/21; C12N 2501/2306; C12N 2501/515; C12N 2501/58; C12N 2501/602; C12N 2501/603; C12N 2501/604; C12N 2501/605; C12N 2501/606; C12N 2501/608; C12N 2502/1121; C12N 2502/1329; C12N 2506/1307; C12N 2506/1315; C12N 2510/02; C12N 2511/00; C12N 2533/50; C12N 2533/72; C12N 2533/74; C12N 2740/16043; C12N 2760/18434; C12N 2760/18534; C12N 2800/22; C12N 2800/80; C12N 2820/007; C12N 2830/001; C12N 2830/008; C12N 2830/15; C12N 2830/20; C12N 2840/007; C12N 2840/60; C12N 5/0602; C12N 5/0636; C12N 5/0657; C12N 5/0677; C12N 5/0696; C12N 9/1096; C12N 9/1211; C12N 9/22; C12N 9/2408; C12N 9/90; G06K 9/00147; G06K 9/00127; G06K 9/4604; G06K 9/6255; C12Q 1/70; C12Q 1/6897; C12Q 2565/601; G01B 15/00; G01B 21/28; C07K 2317/34; B01J 20/28078; B01J 20/28088; B01J 20/28095; A61K 2039/5258; A61K 39/00; C25B 11/031; C25B 11/02; Y02C 20/40; B82Y 30/00; B82Y 5/00; Y10T 29/4981; H01Q 15/0086

See application file for complete search history.

(56) References Cited

U.S. PATENT DOCUMENTS

2013/0191037 A1    7/2013  Mulder et al.

OTHER PUBLICATIONS

Havlik et al. Analytical Chemistry 2015, vol. 87, No. 17, pp. 8657-8664.*
Vironova, Characterization of AAV samples using TEM, published on Feb. 17, 2016.*

(Continued)

*Primary Examiner* — Bao Q Li
(74) *Attorney, Agent, or Firm* — Fasth Law Offices; Rolf Fasth

(57) ABSTRACT

The method is for quantitative measurement of particle content using hydrated state imaging such as CryoTEM. A sample of virus-like particles (VLPs) or virus particles is provided. Preferably, the sample is rapidly frozen into a cryogenic liquid at a cryogenic temperature. While at the cryogenic temperature, the particle content of each VLP in the frozen sample is observed in the CryoTEM. An amount of the particle content of the VLPs is determined to assess whether the VLPs are empty or not.

9 Claims, 1 Drawing Sheet

(56) References Cited

OTHER PUBLICATIONS

Rolfdao et al. Expert Rev. Vaccines 2010, vol. 9 (10), pp. 1149-1176.*
Sommer, JM et al, Quantification of Adeno-Associated Virus Particles and Empty Capsids by Optical Density Measurement. Molecular Therapy, Jan. 2003, vol. 7, No. 1: pp. 122-128, p. 125, 1st col. 11st paragraph, p. 126, 1st col. 1st paragraph, p. 127, 1st col. 3rd paragraph.

* cited by examiner

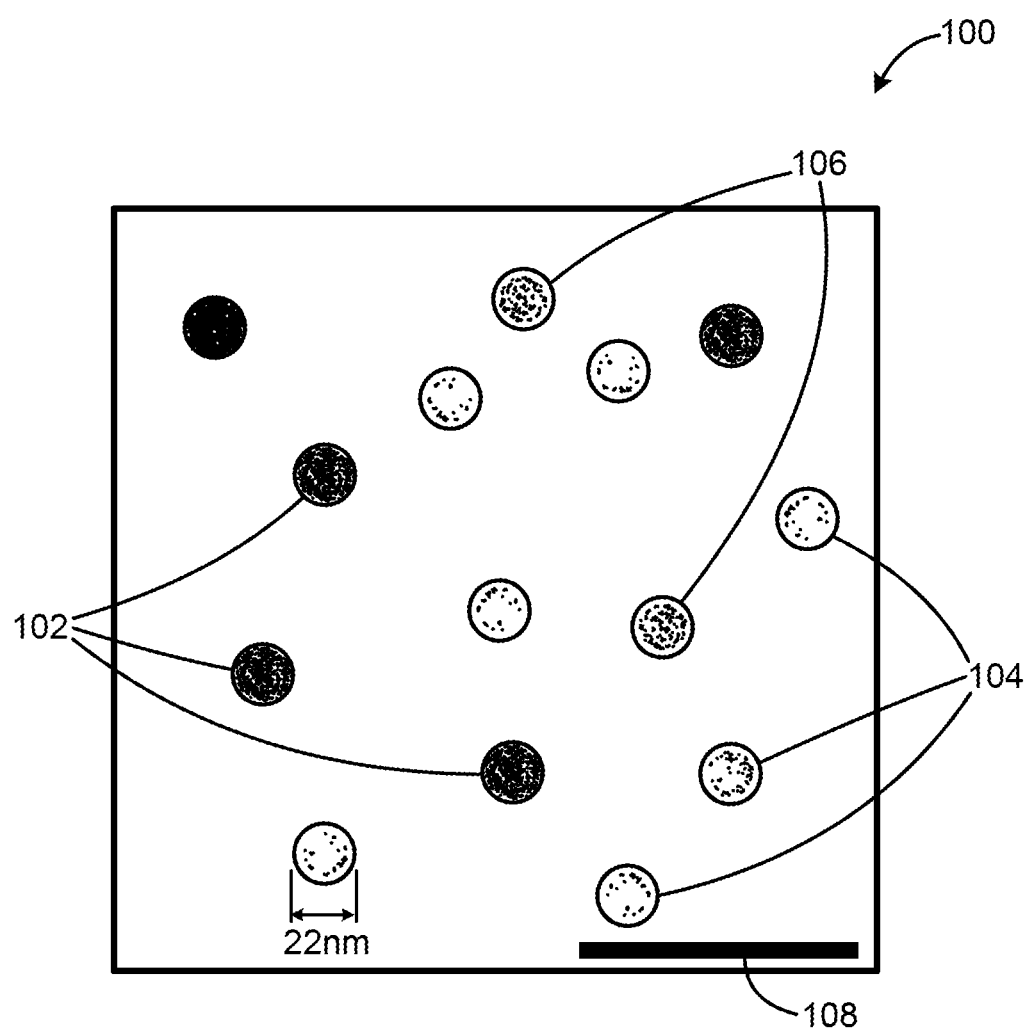

METHOD OF QUANTITATIVE MEASUREMENT OF PARTICLE CONTENT USING HYDRATED STATE IMAGING

PRIOR APPLICATION

This application is a U.S. national phase application based on International Application No. PCT/US2018/015263, filed 25 Jan. 2018, claiming priority from U.S. Provisional Patent Application No. 62/465,981, filed 2 Mar. 2017.

TECHNICAL FIELD

The invention relates to a method of quantitative measurement of particle content by using a hydrated state imaging method such as CryoTEM (Cryo Transmission Electron Microscopy).

BACKGROUND AND SUMMARY OF THE INVENTION

In the pharmaceutical industry, Virus-Like Particles (VLPs) and wild-type (wt) or modified viruses, for example, Adeno Associated Virus (AAV) particles are extensively used as a carrier for gene delivery. In general, VLPs or replication deficient AAVs cannot replicate/reproduce as opposed to real virus particles and are often preferred as a carrier for gene delivery. The assessment of their content of genetic material is of prime importance as it is directly linked to the efficiency of the treatment. Different methods are commonly used to assess the content of Virus-Like Particles (VLPs) and AAV particles. One method is real-time polymerase chain reaction, also known as quantitative polymerase chain reaction (qPCR). Historically, negative-stain Transmission Electron Microscopy (nsTEM) has been used as an orthogonal direct method used as a reference to visualize the content of VLPs and AAV particles. One reason for this is that nsTEM is fast, simple and provides a good resolution so the VLP and AAV particles can actually be seen. Another is that nsTEM has been considered accurate and a good method for determining particle content. However, it was recently discovered that nsTEM has inherent characteristics that makes it unreliable, not robust, and even erroneous when it comes to assessing the content of VLPs, AAV particles and wt virus particles.

In nsTEM, stain is applied to the sample before or after the sample is applied on the grid to enhance the contrast and protect the particles. One drawback of nsTEM is that the stain covers the particles and does not necessarily penetrate the particles. This prevents the direct native viewing of the content of the particles. That is, the stain makes the analysis of the content of particles in nsTEM an indirect method. In other words, the stain only enters the particles and creates contrast representing the interior of the particles when there is an opening in the particle shells, for example, when the particles are broken. The stain might also adversely affect the morphology of the sample, and due to the blotting steps (removing access liquid using a filter paper) and the low pH of the stain solution, it was surprisingly realized that particles are often spatially locally affected by the preparation. It was unexpectedly discovered that the thickness of the stain layer cannot be fully controlled in the preparation procedure and in regions with thinner stain the particles are not well protected. It turns out that the shape of empty particles is sometimes affected by the staining and blotting procedure, even if they are intact. The preparation procedure can create a dent or invagination on the shell at the top of the particle where stain can assemble. This is more likely for empty particles since the interior content then does not help to retain the shape. This makes it look empty in the microscope whereas in regions with thicker stain, the particle shape is intact and there is no visible difference between an empty and filled intact particle. This makes the analysis difficult and unreliable.

In nsTEM, the particles are conventionally seen, classified and counted as empty if they appear with a bright outer fringe and a dark internal part. The rationale is that once on the grid, an empty particle collapses and the stain fills the hollow parts. Full particles are those appearing as bright disks with slightly brighter parts at the center. The rationale is that since the particles are filled, they do not collapse during the preparation and therefore have no hollow part. There are often a large portion of the particles that cannot be unambiguously classified. They are so called uncertain particles.

Another problem is that when an empty particle does not collapse during preparation, it appears as filled while, on the other hand, when a filled particle collapses, due to high mechanical constrains on a local level, it may collapse and appear as empty. An important insight of the present invention is the realization that the method of using nsTEM is prone to a high number of false positives and false negatives.

There is a need for a better and a more reliable way of quantifying particle content. The method of the present invention is a reliable method by which the content of VLPs, AAVs and wt viruses can be assessed with good robustness, accuracy, repeatability and specificity. More particularly, the method is for quantitative characterization of the content of VLPs, AAVs and wt virus particles by imaging them in their native hydrated state such as by using Cryo Transmission Electron Microscopy (CryoTEM). It was also discovered that the analysis can reliably be done by using ionic liquids to prepare the sample for TEM imaging or using special sample holders for liquid samples (sometimes referred to as liquid TEM or in situ TEM). The ionic liquid preparation method is similar to CryoTEM in that the addition of the ionic liquid keeps the particles in a hydrated state so there is no need to use stain to enhance the contrast. However, a small amount of stain or chemical can beneficially be added to preserve the structure of the particles.

The method of the present invention provides a solution to the above-outlined problems. More particularly, the method is for quantitative measurement of particle content using imaging. A sample of virus-like particles (VLPs) or virus particles is provided. The sample is prepared to maintain the sample in a hydrated state. The particle content of each VLP or virus particle in the sample is observed in an imaging device. An amount of the particle content is determined to assess whether the VLPs or virus particles are empty (104), full (102) or ambiguous (106). More particularly, the method is for the quantitative measurement of the particle content of particles by using a hydrated state imaging method such as CryoTEM. A sample of virus or virus-like particles (VLPs), such as AAV particles, or virus-particles is provided. The sample is prepared to maintain the sample in a hydrated state. This may be done in several ways. For CryoTEM in a preferred embodiment, the sample is rapidly frozen into a cryogenic liquid at a cryogenic temperature. While at the cryogenic temperature, a particle content of each VLP in the frozen sample is observed in the CryoTEM imaging device. For other hydrated state imaging methods, the imaging is performed in a TEM imaging device but not at cryogenic temperatures, by using liquid sample holders, or by adding an ionic liquid to the sample at preparation. A measurement of the particle content is determined to assess whether the VLPs are empty or not.

In an alternative embodiment, the method further comprises the step of automatically or manually detecting particles in the images and displaying detected particles on a display and automatically or manually deleting particles that are smaller than a lower size limit and larger than an upper size limit. It is also possible to automatically or manually remove or add particles to the image without first displaying the particles. It is also possible to display VLPs or virus particles and interactively delete or add VLPs or virus particles to the image.

In another alternative embodiment, the method further comprises the step of automatically or manually classifying a particle that has an inner density with no distinct boundary between a particle shell and a particle core as a filled particle.

In yet an alternative embodiment, the method further comprises the step of automatically or manually classifying a particle that has a distinct outer shell and a minute internal density as an empty particle.

In an alternative embodiment, the method further comprises the step of using Cryo Transmission Electron Microscopy to determine the particle content of the VLPs.

In another alternative embodiment, the method further comprises the step of determining the particle content of adeno associated virus (AAV) particles.

In yet an alternative embodiment, the method further comprises the step of using the AAV particles as a carrier for gene delivery.

In an alternative embodiment, the method further comprises the step of classifying AAV particles that contain one or more copies of a gene as a filled particle.

In yet another alternative embodiment, the method further comprises the step of classifying AAV particles that contain no gene as an empty particle.

In another embodiment, the method further comprises adding an ionic liquid to the sample to keep the VLPs in a hydrated state.

In another embodiment, the method further comprises imaging the VLP particles in their native, liquid and hydrated state by using a liquid sample holder.

BRIEF DESCRIPTION OF DRAWING

FIG. 1 is a schematic image from an AAV specimen observed by CryoTEM.

DETAILED DESCRIPTION

The present invention relates to a method of using a hydrated state imaging method such as CryoTEM to assess and quantitatively measure the degree of content in the interior of VLPs, AAV particles and wt virus particles. The particle content measurement could be a metric (number) that corresponds to how full or empty the particle is. It could e.g. be a measurement of the overall intensity of the particle interior, or the intensity normalized with the intensity on the shell of the particle. It could also be a measure of how much of the area inside the particle that is bright or dark.

As mentioned above, an important aspect of the present invention is the realization and discovery that nsTEM is not suitable for the assessment/analysis of filled/empty particles due to the fact that the particle appearance when imaged on the grid depends on several parameters such as:

The thickness of the stain (which varies throughout the grid);

The extent to which the specimen is dried (which varies throughout the grid); and The integrity of the particles (which may or may not be affected by the staining process and preparation process due to local variations in the mechanical stress the particles undergo).

Because the stain thickness influences the appearance of the particles it also affects the result. The stain thickness varies over the grid and this cannot be reliably controlled. For example, when the stain is relatively thin, the particles are more exposed to physical forces in the preparation and some particles may cave so that the stain is contained in the cave without penetrating into the inside of the particle. When the stain remains in the cave of the particle, it gives an appearance that is very similar to that of empty particles that have been filled by the stain. The particle content analysis thus depends a lot on whether particles in regions with thick or thin stain are imaged and analyzed. As a result of the uneven distribution of the stain on the particles when nsTEM is used, the particles often appear as having different amounts of content although they, in reality, have not. This is an insight that has not been realized in the past.

By using CryoTEM instead, the appearance of the particles cannot be disadvantageously affected by an uneven distribution of the stain (since no stain is used) so the particles tend to look the same in all areas of the viewing area which makes CryoTEM very effective for the content analysis of the present invention. In other words, although it is more complicated to use CryoTEM compared to nsTEM for content analysis, it was unexpectedly discovered that the advantages of the more accurate results outweigh the drawbacks of using the more cumbersome CryoTEM technique. In CryoTEM, according to the method of the present invention, a small aliquot of a sample is deposited onto a hydrophilized copper grid covered with a thin carbon film. The excess of the sample is then blotted-off by using filter paper. The grid is then rapidly, and before the sample dries out, plunged into a cryogenic liquid where the sample of particles is instantly frozen. The rapid freezing allows the sample/specimen to be embedded in amorphous ice close to its native (i.e. unstained) hydrated form so the particles has the correct appearance everywhere in the sample since they are not affected by any stain. The specimen is then kept at cryogenic temperatures during the whole process while being inserted and observed in the transmission electron microscope. One advantage of the method of the present invention is that it allows a direct visualization of unaltered particles with the possibility of seeing their internal features. This makes it possible to make a more correct assessment of whether a particle is empty or not. In CryoTEM, empty particles appear as disks that has a minute internal density. One explanation is that the internal parts of particles can be seen using CryoTEM and empty particles have a low internal density. Filled particles appear as dark homogeneous disks. Again, the internal parts of particles can be seen using CryoTEM, and filled particles that contain genetic material inside, have a homogeneous internal density.

EXAMPLE

Below is a detailed example of how CryoTEM is used to carry out the method of the present invention.

Grid Preparation

Suitable grids, such as 400 mesh copper (Cu) grids, were first hydrophilized. This was done by glow-discharging the grids. More particularly, the copper grids, covered with a carbon film, were placed in a glow discharger. Vacuum was applied until the pressure reached about 0.5 mbar in the chamber. A current was applied, such as about 20 mA, for about 1 minute. The pressure was then increased to ambient pressure. The grids were removed and the glow-discharger was turned off.

Grid Freezing

A plunge freezer was turned on. The sample chamber was equilibrated to the desired temperature and humidity. The blot paper in the sample chamber was changed. An ethane bath in the cooling station was prepared. A freshly glow-discharged grid was loaded on the tweezers. The freezing process was started. About 3 μL of the sample was deposited on a grid. After about 10 seconds of wait time, the grid was blot with filter paper and plunge-frozen. The grid was transferred in a cryo-grid box and stored in liquid nitrogen.

The ethane and liquid nitrogen were safely thawed and the plunge-freezer was turned off.

Grid Transfer

The cryo-grid box was transferred from its storage location into a cryo-work station precooled with liquid nitrogen, into which a cryo-holder preliminary pump was inserted. The grid was transferred to the grid slot on the cryo-holder. The cryo-holder was inserted into the CryoTEM and the liquid nitrogen container was filled.

Grid Imaging

In the grid imaging step, it was important to make sure the microscope had been correctly aligned according to the protocol described by the manufacturer, and that the blank image from the camera was flat. (It is to be understood that the grid imaging step may be done automatically where images are acquired automatically without requiring an operator to be sitting at the microscope to acquire the images. The grid is screened until finding a suitable area.) The magnification was then set with a field of view of about 600-1000 nm. The focus 0 was found before setting the microscope at a slight defocus of about 6 μm. This defocusing step could have been done manually or automatically in microscopes that have autofocus and defocus functionality. The image was acquired and moved to a nearby area. The step of acquiring the image was repeated until the desired number of images was acquired.

Subsequent Image Treatment and Analysis

The images were saved and imported by suitable analysis software such as Vironova Analyzer Software (VAS). The images to be saved in the microscope were selected and saved in a suitable format such as in 16 bit tiff format, or alternatively automatically saved after the automatic image acquisition. A folder corresponding to the project in VAS was created and all the required information in the different nodes was completed.

The images were imported in the "Microscopy" node by right clicking on the node, selecting "Open image(s)" and choosing the appropriate files prior to clicking on "Open".

Particle Detection and Classification

In the "Microscopy" node, in the "Particle Type" field, the "VLP(cryo)" was entered. The images in which particles were to be detected were selected before right-clicking on one of them. A "Run detection . . . " was chosen. The following parameters were entered:

| Detection algorithm Parameter | Ellipse segmentation | |
|---|---|---|
| | Recommended Nominal Value | Acceptable Range |
| Clear Content of Detected Particle | Yes | Yes |

-continued

| Detection algorithm Parameter | Ellipse segmentation | |
|---|---|---|
| | Recommended Nominal Value | Acceptable Range |
| Dark membranes | Yes | Yes |
| Divide Large Components | Yes | Yes |
| Edge Gap Tolerance | 0.2 | 0.2 |
| Edge Width (nm) | 5 | 4-6 |
| Maximum Diameter (nm) | 24 | 22-30 |
| Minimum Diameter (nm) | 18 | 16-22 |
| Minor Axis Ratio | 0.2 | 0.2 |
| Output shape | Circular | Circular |
| Post Processing Refinement | Yes | Yes |
| Prefer Circular Ellipses | Yes | Yes |
| Pre-processing method | EdgeDetection | EdgeDetection |

The detected particles were displayed on the Plot Control by using the scatterplot display, with "Size" on the x axis, and "Signal-To-Noise" on the y axis. The detected particles with a signal to noise <0.1 were first selected before deleting them.

The detected particles with a size <17 nm and >28 nm were then selected before deleting them also. The images were visually assessed on the screen and falsely and incorrectly detected AAV particles were removed. The correctly detected particles were accepted by using the verify tool. The AAV particles that were not detected by the automated detection were manually boxed.

In more general terms, the following analysis steps were performed:

1) The particles of interest in the images were detected either manually or by using a suitable detection algorithm (for example, template matching, circular object detection, region or border-based detection methods etc.);

2) False detections, based on measures of size, shape and the signal to noise ratio for each particle, were removed (automatically or manually or a combination of both); and 3) If necessary, particles that were not detected were added if an automated detection algorithm was used.

Particle Classification

In the particle class node of the Plot control toolbar, "Content" was chosen. All the detected particles were displayed by using the RDP PCA tool in the Plot control toolbar. The plot was rotated in order to obtain a clear separation between two clusters. The particles of one cluster were selected and assigned their corresponding class. The class was determined by using the following parameters:

AAV particles displaying an inner density with no distinct boundary between the shell and the core were classified as filled particles; and AAV particles displaying a distinct outer shell and minute internal density were classified as empty particles.

The particles from the other cluster were then selected and assigned their corresponding class. All the images were visually analyzed to assess the classification. The class "Uncertain" was assigned to all particles in which a discrepancy was found between the analyst's assessment and the semi-automated classification.

In more general terms, the following steps were performed:

1) The content of the particles was measured by analysing the overall intensity and intensity distribution inside the particles; and 2) The particles were classified based on these measurements. This could have been done in several ways such as by manually thresholding each measured feature (e.g. if darker than a certain intensity Tf then classify as full, if brighter than another intensity Te then classify as empty and if between Tf and Te then classify as uncertain). It could also have been done by marking groups of particles in scatterplots of the features or by using automatic/semiautomatic clustering and classification methods.

It is possible to, in a fully automated fashion, discriminate between filled and empty particles by looking at the internal density profile of the particles.

FIG. 1 is a schematic illustration of a typical image of VLPs from an AAV specimen 100 observed by CryoTEM. The specimen contains filled particles 102 that appear as plain dark disks.

The particles 102 are thus filled with, for example, a pharmaceutical substance or a gene. Empty particles 104 appear as dark circles with a bright internal intensity corresponding to low internal density because they contain or carry no gene. Particles 106 for which the classification is ambiguous appear to display characteristics of in between filled and empty particles. The analysis thus determines both the quantity/number of particles that contain the pharmaceutical substance (gene) and also how much each particle is filled with the pharmaceutical substance or gene. Some particles may only be partially filled with a pharmaceutical substance whereas for genes, the particles either contain one or more copies of the gene or are empty. The scale bar 108 of FIG. 1 represents 100 nm.

While the present invention has been described in accordance with preferred compositions and embodiments, it is to be understood that certain substitutions and alterations may be made thereto without departing from the spirit and scope of the following claims.

We claim:

1. A method for assessing a particle interior content using imaging, comprising:
    providing a sample of adeno associated virus (AAV) particles;
    maintaining the sample in a native unstained hydrated state;
    imaging the sample in the native unstained hydrated state in a Cryo Transmission Electron Microscopy (CryoTEM);
    observing the particle interior content of each AAV particle in the sample in acquired images in the CryoTEM; and
    based on the observation of the particle interior content, measuring an intensity of the particle interior content of each AAV particle in the sample;
    based on the measured intensity, determining an amount of the particle interior content of each AAV particle in the sample and assessing whether the AAV particles are empty, full or ambiguous.

2. The method according to claim 1 wherein the method further comprises the step of automatically or manually detecting particles in images and deleting particles that are smaller than a lower size limit and larger than an upper size limit.

3. The method according to claim 2 wherein the method further comprises displaying AAV particles and interactively deleting or adding AAV particles to the image.

4. The method according to claim 1 wherein the method further comprises the step of classifying a particle that has an inner density with no distinct boundary between a particle shell and a particle core as a filled particle.

5. The method according to claim 1 wherein the method further comprises the step of classifying a particle that has a distinct outer shell and a minute internal density as an empty particle.

6. The method according to claim 1 wherein the method further comprises the step of classifying AAV particles that contain a gene as a filled particle.

7. The method according to claim 6 wherein the method further comprises the step of classifying AAV particles that contain no gene as an empty particle.

8. The method according to claim 1 wherein the method further comprises adding an ionic liquid to the sample to keep the AAV particles in a hydrated state.

9. The method according to claim 1 wherein the method further comprises imaging the sample in a hydrated liquid state by using a liquid sample holder.

* * * * *